(12) United States Patent
Chou et al.

(10) Patent No.: US 10,377,714 B2
(45) Date of Patent: Aug. 13, 2019

(54) TRANS-ISOMERIC HETEROCYCLIC COMPOUNDS AND PREPARATION THEREOF

(71) Applicant: TaiGen Biotechnology Co., Ltd., Taipei (TW)

(72) Inventors: Shan-Yen Chou, Taipei (TW); Wen-Chang Chen, Yilan (TW); Chi-Feng Yen, Taipei (TW); Han-Pei Hsu, Taipei (TW); Ming-Chu Hsu, Santa Clara, CA (US); Chu-Chung Lin, Taipei (TW)

(73) Assignee: TaiGen Biotechnology Co., Ltd., Taipei (TW)

( * ) Notice: Subject to any disclaimer, the term of this patent is extended or adjusted under 35 U.S.C. 154(b) by 0 days.

(21) Appl. No.: 15/674,937

(22) Filed: Aug. 11, 2017

(65) Prior Publication Data

US 2019/0047956 A1 Feb. 14, 2019

(51) Int. Cl.
*C07D 211/60* (2006.01)

(52) U.S. Cl.
CPC ........ *C07D 211/60* (2013.01); *C07B 2200/09* (2013.01); *C07B 2200/13* (2013.01)

(58) Field of Classification Search
None
See application file for complete search history.

(56) References Cited

U.S. PATENT DOCUMENTS

2001/0056186 A1 12/2001 Giffels et al.

FOREIGN PATENT DOCUMENTS

| WO | WO-2012/036997 A1 | 3/2012 |
| WO | WO-2012/101063 A1 | 8/2012 |
| WO | WO-2015/091584 A1 | 6/2015 |

OTHER PUBLICATIONS

Deninno et al "1,5-Substituted Nipecotic Amides: Selective PDE8 Inhibitors Displaying Diastereomer-Dependent Microsomal Stability" Bioorganic and Medicinal Chemistry Letters vol. 21, pp. 3095-3098, 2011.

Irfan et al "Continuous Flow Hydrogenation of Functionalized Pyridines" European Journal of Organic Chemistry vol. 2009, pp. 1327-1334, 2009.

*Primary Examiner* — Heidi Reese
(74) *Attorney, Agent, or Firm* — Cesari and McKenna, LLP

(57) ABSTRACT

A trans-isomeric compound of formula (I) below or a pharmaceutically acceptable salt thereof:

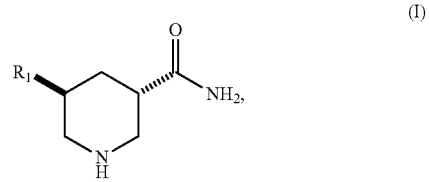

(I)

in which $R_1$ is $C_1$-$C_5$ alkyl or $C_3$-$C_5$ cycloalkyl and the trans-isomeric compound has a trans:cis ratio of at least 70:30. Further disclosed is a method for preparing the trans-isomeric compound.

28 Claims, No Drawings

TRANS-ISOMERIC HETEROCYCLIC COMPOUNDS AND PREPARATION THEREOF

FIELD OF THE INVENTION

The present invention relates to trans-isomeric heterocyclic compounds, i.e., piperidines, and a method of preparing these stereo-specific isomers.

BACKGROUND

Some heterocyclic compounds, e.g., piperidines, possess pharmaceutical activity. It has been reported that their pharmaceutical activity, as well as safety, varies based on the stereochemical configurations of the substituents on the piperidine ring. See, e.g., Pharmacia, 1989, 25(4), 311-336. Thus, effective synthesis of piperidines with high stereoselectivity is of great importance.

Methods for preparing cis/trans mixtures of piperidines, e.g., piperidine-3-carboxamide, are well known in the field. See, e.g., DeNinno et al., Bioorganic and Medicinal Letters, 2011, 21, 3095-3098; and Gancia et al., WO 2015/091584. Yet, conventional methods produce either non-stereo selective isomers or mainly cis-isomers.

There is a need to develop a new method for preparing trans-isomeric piperidines.

SUMMARY

An aspect of the present invention is a method of preparing a trans-isomeric compound of formula (I) below or a pharmaceutically acceptable salt thereof:

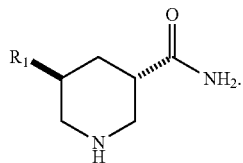

(I)

The method, unexpectedly producing trans-isomeric piperidines in high yield and high stereo-selectivity, includes the step of hydrogenating a compound of formula (II) below or a pharmaceutically acceptable salt thereof:

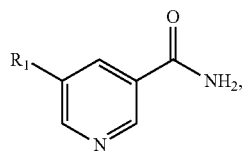

(II)

with a palladium catalyst in the presence of an inert solvent to obtain a trans-isomeric compound of formula (I) having a trans:cis ratio of at least 70:30 (up to 99.9:0.1) or a pharmaceutically acceptable salt thereof, in which $R_1$ in formulas (I) and (II) is $C_1$-$C_5$ alkyl or $C_3$-$C_5$ cycloalkyl.

The above-described method can further include a resolution step, which is performed via optical resolution of the trans-isomeric compound with an acidic resolving agent. This process can provide an optically enriched enantiomer of the trans-isomeric compound of formula (I) or a pharmaceutically acceptable salt thereof. The acidic resolving agent can be in R-form or S-form. If needed, the enantiomer thus obtained can be recrystallized with a recrystallization solvent.

Another aspect of this invention is a trans-isomeric compound of formula (I) below or a pharmaceutically acceptable salt thereof:

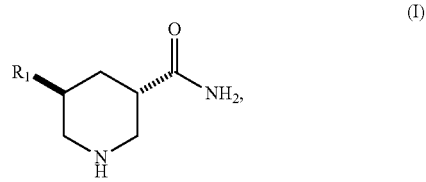

(I)

in which $R_1$ is $C_1$-$C_5$ alkyl or $C_3$-$C_5$ cycloalkyl and the trans-isomeric compound has a trans:cis ratio of at least 70:30. Typically, $R_1$ is $C_1$-$C_5$ alkyl, e.g., methyl.

The trans-isomeric compound of formula (I) can be in the form of (3S, 5S)-configuration, i.e., formula (Ia) shown below, or (3R, 5R)-configuration, i.e., formula (Ib) also shown below:

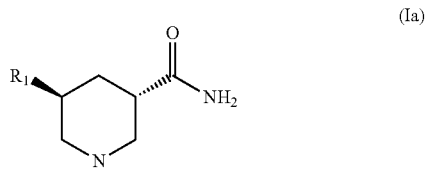

(Ia)

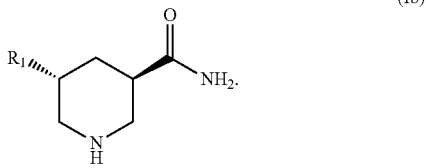

(Ib)

The term "$C_1$-$C_5$ alkyl" herein refers to a straight or branched chain hydrocarbon radical containing 1 to 5 carbon atoms. Examples of $C_1$-$C_5$ alkyl include, but are not limited to, methyl, ethyl, propyl, and isopropyl. The term "$C_3$-$C_5$ cycloalkyl" refers to a saturated, cyclic hydrocarbon moiety containing 3 to 5 carbon atoms. Examples of $C_3$-$C_5$ cycloalkyl include, but are not limited to, cyclopropyl, cyclobutyl, and cyclopentyl. Alkyl and cycloalkyl mentioned herein include both substituted and unsubstituted moieties, unless specified otherwise. Possible substituents on alkyl and cycloalkyl include, but are not limited to, amino, hydroxyl, halo, thio, acylamino, aminoacyl, aminothioacyl, amidino, guanidine, ureido, cyano, nitro, nitroso, azido, acyl, thioacyl, acyloxy, carboxyl, and carboxylic ester.

A further aspect of this invention is a trans-isomeric compound of formula (I) prepared by the method described above.

The details of the invention are set forth in the description below. Other features, objects, and advantages of the invention will be apparent from the following detailed description of several embodiments, and also from the appending claims.

DETAILED DESCRIPTION

Disclosed first in detail herein is a trans-isomeric compound of formula reproduced below, or a pharmaceutically acceptable salt thereof:

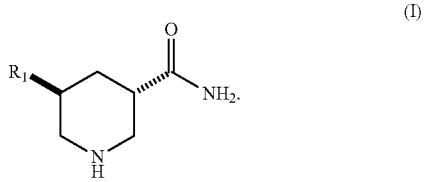

(I)

In this formula, $R_1$ is $C_1$-$C_5$ alkyl or $C_3$-$C_5$ cycloalkyl. Typically, $R_1$ is $C_1$-$C_5$ alkyl, e.g., methyl, ethyl, and isopropyl. Of note, the trans-isomeric compound has a trans:cis ratio of at least 70:30, e.g., 80:20, 90:10, and 99:1.

The trans-isomeric compound can be present as a pure enantiomer. An exemplary enantiomer is in the form of (3S, 5S)-configuration of formula (Ia) shown in the SUMMARY section above or a pharmaceutically acceptable salt thereof, or in the form of (3R, 5R)-configuration of formula (Ib), also shown in the SUMMARY section above, or a pharmaceutically acceptable salt thereof.

The term "pharmaceutically acceptable salt" refers to an acid or base salt of a compound of this invention. Preferred pharmaceutically acceptable salts include acid addition salts that can be formed by reacting the compound with a pharmaceutically acceptable acid, such as hydrochloric acid, hydrobromic acid, hydrofluoric acid, sulfuric acid, nitric acid, phosphoric acid, formic acid, acetic acid, propionic acid, oxalic acid, malonic acid, succinic acid, maleic acid, lactic acid, malic acid, tartaric acid, citric acid, picric acid, methanesulfonic acid, benzenesulfonic acid, aspartic acid, and glutamic acid.

The compounds described above include the compounds themselves, as well as their salts, prodrugs, polymorphs, stereoisomers and solvates, if applicable. A salt, for example, can be formed between an anion and a positively charged group (e.g., amino) on a compound having one of the above formulas. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound having one of the above formulas. Suitable cations include sodium ion, potassium ion, magnesium ion, calcium ion, and an ammonium cation such as tetramethylammonium ion. The compounds also include those salts containing quaternary nitrogen atoms. For calculation simplicity, unless otherwise stated, the weight of a compound mentioned herein refers to that of the free base form of that compound. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Also within the scope of this invention is a method of preparing a trans-isomeric compound of formula (II) or a pharmaceutically acceptable salt thereof.

To reiterate, the method includes hydrogenating a compound of formula (II), shown in the SUMMARY section above, with a palladium catalyst in the presence of an inert solvent to stereo-selectively produce a trans-isomeric compound of formula (I) having a trans:cis ratio of at least 70:30 or a pharmaceutically acceptable salt thereof.

The stereo-selective hydrogenation of the compound of formula (II) is conducted in the presence of a palladium catalyst at a suitable pressure using a variety of solvents. The trans:cis ratios are determined by nuclear magnetic resonance (NMR) spectroscopy.

The palladium catalyst includes one or more palladium compounds, such as $Pd(OH)_2/C$, $Pd/C$, $Pd(OAc)_2$, $Pd/Al_2O_3$, or a combination thereof. It optionally contains another transition metal catalyst, e.g., Pt/C and Rh/C. The content of palladium in the palladium catalyst can be about 0.01 wt % to about 30 wt %, or about 0.1 wt % to about 25 wt %, or about 1 wt % to about 20 wt %, or about 2 wt % to about 20 wt %, or about 5 wt % to about 20 wt %.

Examples of the inert solvent include, but are not limited to, $H_2O$, a $C_1$-$C_{10}$ ester (e.g., ethyl acetate and methyl acetate), a $C_3$-$C_{10}$ cycloalkane (e.g., cyclopropane, cyclobutane, cyclopentane, and cyclohexane), tetrahydrofuran (THF), dimethylformamide (DMF), acetonitrile, a $C_1$-$C_{10}$ alcohol (e.g., methanol, ethanol, n-propanol, isopropanol, n-butanol, isobutanol, t-butanol, ethylene glycol, propylene glycol, and butylenes glycol), an alkylene glycol monoalkyl ether (e.g., propylene glycol monomethyl ether, propylene glycol monoethyl ether, and propylene glycol monopropyl ether), an alkylene glycol monoalkyl ether carboxylate (e.g., propylene glycol monomethyl ether acetate, propylene glycol monoethyl ether acetate, and propylene glycol monopropyl ether acetate), an amide-based solvent (e.g., N,N-dimethylacetamide and N,N-dimethylformamide), an organic acid (e.g., a $C_1$-$C_{10}$ carboxylic acid and a $C_1$-$C_{10}$ sulfonic acid), and combinations thereof. Of note, an inert solvent can contain two or more $C_1$-$C_{10}$ esters, two or more $C_3$-$C_{10}$ cycloalkanes, and the like. Optionally, an inert solvent can contain one or more inorganic acids (e.g., hydrochloric acid, sulfuric acid, phosphoric acid, and nitric acid).

Preferably, the inert solvent is $H_2O$, a $C_1$-$C_5$ ester, a $C_3$-$C_6$ cycloalkane, THF, DMF, acetonitrile, a $C_1$-$C_5$ alcohol, propylene glycol monomethyl ether, propylene glycol monomethyl ether acetate, N,N-dimethylacetamide, a $C_1$-$C_5$ carboxylic acid (e.g., formic acid, acetic acid, propionic acid, butyric acid, isobutyric acid, difluoroacetic acid, trifluoroacetic acid, and a combination thereof), a $C_1$-$C_5$ sulfonic acid (e.g., methanesulfonic acid), or a combination thereof, optionally containing one or more inorganic acids of hydrochloric acid, sulfuric acid, phosphoric acid, and nitric acid. More preferably, the inert solvent is $H_2O$, a $C_1$-$C_5$ ester, a $C_3$-$C_6$ cycloalkane, THF, DMF, a $C_1$-$C_5$ alcohol, propylene glycol monomethyl ether, propylene glycol monomethyl ether acetate, N,N-dimethylacetamide, a $C_1$-$C_5$ carboxylic acid, a $C_1$-$C_5$ sulfonic acid, or a combination thereof, optionally containing hydrochloric acid. Among the most preferred inert solvents are $H_2O$, methanol (MeOH), ethanol (EtOH), isopropanol (i-PrOH), ethyl acetate, formic acid, acetic acid, methanesulfonic acid, and a combination thereof, optionally containing hydrochloric acid.

Unexpectedly, the inert solvent containing an inorganic acid (e.g., hydrochloric acid, sulfuric acid, phosphoric acid, and nitric acid) is capable of providing extremely high stereo-selectivity of trans-isomeric piperidines. As examples, the inert solvent is an organic acid or a combination of the organic acid with one or more of the following solvents: $H_2O$, a $C_1$-$C_{10}$ ester, a $C_3$-$C_{10}$ cycloalkane, THF, DMF, acetonitrile, an alkylene glycol monoalkyl ether, an alkylene glycol monoalkyl ether carboxylate, an amide-based solvent, a $C_1$-$C_{10}$ alcohol, and an inorganic acid. Preferably, the inert solvent is a $C_1$-$C_5$ carboxylic acid, a $C_1$-$C_5$ sulfonic acid, or a combination thereof, optionally combined with one or more solvents of $H_2O$, a $C_1$-$C_{10}$ ester, a $C_3$-$C_{10}$ cycloalkane, THF, DMF, acetonitrile, an alkylene glycol monoalkyl ether, an alkylene glycol monoalkyl ether carboxylate, an amide-based solvent, a $C_1$-$C_{10}$ alcohol, and an inorganic acid. More preferably, the inert solvent is formic acid, acetic acid, propionic acid, butyric acid, isobutyric acid, or a combination thereof, optionally combined with one or more solvents of $H_2O$, a $C_1$-$C_{10}$ ester, a $C_3$-$C_{10}$ cycloalkane, THF, DMF, acetonitrile, an alkylene glycol monoalkyl ether, an alkylene glycol monoalkyl ether carboxylate, an amide-based solvent, a $C_1$-$C_{10}$ sulfonic acid, a $C_1$-$C_{10}$ alcohol, and an inorganic acid.

Also unexpectedly, the inert solvent containing an organic acid (e.g., a $C_1$-$C_5$ carboxylic acid and a $C_1$-$C_5$ sulfonic acid) can produce extremely high stereo-selectivity of trans-isomeric piperidines. As examples, the inert solvent is a $C_1$-$C_5$ ester, a $C_3$-$C_6$ cycloalkane, THF, DMF, acetonitrile, a $C_1$-$C_5$ alcohol, propylene glycol monomethyl ether, propylene glycol monomethyl ether acetate, N,N-dimethylacetamide, a $C_1$-$C_5$ carboxylic acid, a $C_1$-$C_5$ sulfonic acid, or a combination thereof, optionally combined with $H_2O$.

Typically, the hydrogenation reaction is carried out at 10-100° C., e.g., 15-80° C., 20-70° C., 20-60° C., 20-50° C., and 25-45° C. As examples, it is carried out at 25° C., 30° C., 35° C., 40° C., 45° C., 50° C., 55° C., or 60° C.

The hydrogenation reaction can be carried out under a hydrogen pressure of 1-60 bar, 5-50 bar, 10-40 bar, 15-30 bar, or 15-25 bar.

The hydrogenation reaction time varies within a wide range, e.g., 1-80 hours, depending on the palladium catalyst, the hydrogen pressure, the reaction temperature, and the hydrogenation facility used. Completion of the hydrogenation reaction can be confirmed by NMR. After completion, purification can be effected by filtration, concentration under reduced pressure, and distillation. Of note, the trans-isomeric piperidine thus obtained can be converted into a salt form, if needed.

In an exemplary method, the hydrogenation reaction is carried out at 25-45° C. under a hydrogen pressure of 15-25 bar.

By performing the method, trans-isomeric piperidine is typically obtained with a trans:cis ratio of 70:30 to 99.9:0.1 (e.g., 70:30 to 99:1, 70:30 to 95:5, 70:30 to 90:10, 75:25 to 99.9:0.1, 75:25 to 95:5, 75:25 to 90:10, 80:20 to 99.9:0.1, 80:20 to 99:1, 80:20 to 95:5, 80:20 to 90:10, 85:15 to 99.9:0.1, 85:15 to 99:1, 85:15 to 95:5, and 85:15 to 90:10).

The preparation method described above can further include a resolution step, which is performed via optical resolution of the trans-isomeric piperidine thus obtained with an acidic resolving agent. This step provides an optically enriched enantiomer of the trans-isomeric compound of formula (I), i.e., (3S, 5S)- or (3R, 5R)-configuration enantiomer, or a pharmaceutically acceptable salt thereof in high yield and high purity. The acidic resolving agent can be in R-form or S-form. The enantiomer thus obtained can be further recrystallized with a recrystallization solvent.

The term "acidic resolving agent" refers to an acidic compound that can lead to the precipitation of a diastereomer containing a suitable enantiomer in high chemical and optical yields.

Shown below is the optical resolution reaction:

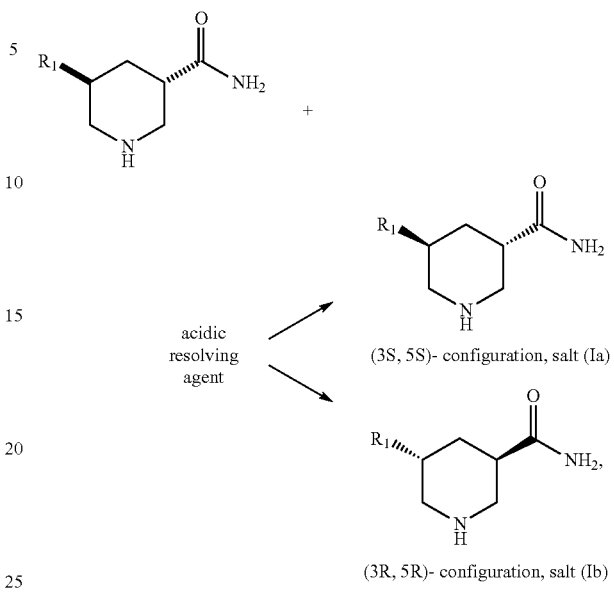

in which $R_1$ is $C_1$-$C_5$ alkyl or $C_3$-$C_5$ cycloalkyl. Two salt forms of the optical isomers containing (3S, 5S)-configuration Ia and (3R, 5R)-configuration Ib can each be obtained by optical resolution of the trans-isomeric compound of formula (I) with an acidic resolving agent.

The enantiomeric excess value (i.e., "ee value") of one enantiomer ((3S, 5S)-configuration Ia or (3R, 5R)-configuration Ib) is 70-100%, 80-100%, 90-100%, 95-100%, 99-100%, 70-99.9%, 80-99.9%, 85-99.9%, 90-99.9%, 95-99.9%, or 99-99.9%. Of note, the term "ee value" is the difference between the amounts of each of the enantiomers present in a mixture, relative to the total amount of the compound in the mixture expressed as percentage (×100%).

The acidic resolving agent can be deoxycholic acid, (−)-2,3:4,6-di-o-isopropylidene-2-keto-L-gulonic acid monohydrate, D-(−)-quinic acid, L-pyroglutamic acid, (−)-monomethylsuccinate, N-acetyl-D-(+)-leucine, N-acetyl-L-methionine, (R)-(+)-N-(1-phenylethyl)succinamic acid, (S)-(+)-5-oxe-2-tetrahydrofurancarboxylic acid, (R)-(+)-N-(1-phenylethyl)phthalamic acid, (−)-mono-(1R)-menthyl phthalate, (−)-menthyloxyacetic acid, (S)-(+)-mandelic acid, L-(+)-tartaric acid, D-(+)-camphoric acid, (−)-dibenzoyl-L-tartaric acid anhydrous, (−)-dibenzoyl-L-tartaric acid monohydrate, (−)-O,O'-dibenzoyl-L-tartaric acid mono (dimethylamide), D-(+)-10-camphorsulfonic acid, L-(+)-lactic acid, L-(−)-malic acid, (−)-O,O'-di-p-toluoyl-L-tartaric acid, (R)-(−)-naproxen, or (S)-ibuprofen.

Note that both R-form and S-form of an acidic resolving agent, e.g., (R)-(−)-naproxen and (S)-(+)-naproxen, can be used to acquire a high ee value.

Preferably, the acidic resolving agent is deoxycholic acid, D-(−)-quinic acid, (−)-monomethylsuccinate, N-acetyl-D-(+)-leucine, N-acetyl-L-methionine, (−)-mono-(1R)-menthyl phthalate, (−)-dibenzoyl-L-tartaric acid anhydrous, (−)-O,O'-dibenzoyl-L-tartaric acid mono(dimethylamide), D-(+)-10-camphorsulfonic acid, L-(+)-lactic acid, or (R)-(−)-naproxen.

The optical resolution can be carried out in the presence of an inert solvent. Use of the inert solvent is well known in the art and varies depending on the type of the starting racemic trans-isomer of a piperidine compound and the resolving agent used.

The inert solvent for optical resolution can be $H_2O$, a $C_1$-$C_{10}$ ester (e.g., ethyl acetate and methyl acetate), a $C_3$-$C_{10}$ cycloalkane (e.g., cyclohexane), THF, DMF, acetonitrile, a $C_1$-$C_{10}$ alcohol (e.g., MeOH, EtOH, n-PrOH, i-PrOH, n-BuOH, and i-BuOH), an alkylene glycol monoalkyl ether (e.g., propylene glycol monomethyl ether, propylene glycol monoethyl ether, and propylene glycol monopropyl ether), an alkylene glycol monoalkyl ether carboxylate (e.g. propylene glycol monomethyl ether acetate, propylene glycol monoethyl ether acetate, and propylene glycol monopropyl ether acetate), an amide-based solvent (e.g. N,N-dimethylacetamide and N,N-dimethylformamide), or a combination thereof.

Preferably, the inert solvent is $H_2O$, acetonitrile, ethyl acetate, $C_1$-$C_3$ alcohol, or a combination thereof. Most preferably, the inert solvent is acetonitrile.

Of note, the ratio of the inert solvent to a reaction substrate is not particularly restricted. For example, the solvent can be used in an amount 0.5 to 100 times the weight of the substrate.

The temperature for optical resolution varies depending on the type of the starting material, the resolving agent, and the solvent used. The reaction is typically performed at 20-60° C. (e.g., 30-50° C.).

The optical resolution described above can further include a step of recrystallization of (3S, 5S)-configuration (Ia) or (3R, 5R)-configuration (Ib) with a recrystallization solvent to form a product with high optical purity.

The recrystallization solvent can be $H_2O$, a $C_1$-$C_{10}$ ester (e.g., ethyl acetate and methyl acetate), a $C_3$-$C_{10}$ cycloalkane (e.g., cyclohexane), THF, DMF, acetonitrile, a $C_1$-$C_{10}$ alcohol (e.g., MeOH, EtOH, n-PrOH, i-PrOH, n-BuOH, and i-BuOH), an alkylene glycol monoalkyl ether (e.g., propylene glycol monomethyl ether, propylene glycol monoethyl ether, and propylene glycol monopropyl ether), an alkylene glycol monoalkyl ether carboxylate (e.g. propylene glycol monomethyl ether acetate, propylene glycol monoethyl ether acetate, and propylene glycol monopropyl ether acetate), an amide-based solvent (e.g. N,N-dimethylacetamide and N,N-dimethylformamide), or a combination thereof. Of note, an anti-solvent can also be employed during recrystallization. The term "anti-solvent" herein refers to a solvent in which a crystalline compound has limited or poor solubility. Examples of the anti-solvent include, but are not limited to, ethyl acetate, acetone, methyl ethyl ketone, toluene, isopropyl acetate, and t-butyl methyl ether.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference in their entirety.

Example 1: Stereoselective Hydrogenation of the 5-methyl-nicotinamide

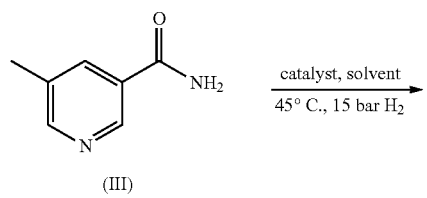

(III)

TABLE 1

Stereo-selective hydrogenation

| Group | Catalyst | Solvent | Ratio (trans:cis) |
|---|---|---|---|
| C1 | 5 wt % Rh/C | EtOH/MeOH | 46:54 |
| C2 | 5 wt % Pt/C | EtOH/MeOH/MsOH | 53:47 |
| E1 | 10 wt % Pd/C | EtOH | 73:27 |
| E2 | 10 wt % Pd/C | EtOH/MeOH/MsOH | 78:22 |
| E3 | 4 wt % Pd/C & 1 wt % Pt/C | EtOH/MeOH/MsOH | 77:23 |
| E4 | 10 wt % Pd(OH)$_2$/C | AcOH | 75:25 |
| E5 | 20 wt % Pd(OH)$_2$/C | i-PrOH | 77:23 |
| E6 | 20 wt % Pd(OH)$_2$/C | H$_2$O/EtOAc | 78:22 |

As shown in the above reaction and Table 1, a magnetically-stirred autoclave was charged with 5-methyl-nicotinamide, i.e., Compound (III), different inert solvents, and transition metal catalysts to afford trans-isomeric Compound (IV). The autoclave was pressurized with $H_2$ at 15 bar and stirred at 45° C. Thereafter, a sample of the contents in the autoclave was analyzed by NMR.

Table 1 indicates that use of a non-palladium catalyst, i.e., Rh/C or Pt/C, resulted in a trans:cis ratio of 46:54 to 53:47 (Groups C1 and C2). In other words, no significant selectivity of diastereoisomers was observed. Unexpectedly, when using a palladium catalyst, the hydrogenation of compound (III) stereo-selectively produced compound (IV) favoring the formation of the trans-isomer with a trans:cis ratio of 73:27 to 78:22 (Groups E1 to E6).

These results indicate that hydrogenation using a palladium catalyst favorably produced trans-isomeric piperidines.

Example 2: Stereo-Selective Hydrogenation of 5-methyl-nicotinamide in the Presence of Formic Acid and Pd(OH)$_2$/C An autoclave was charged with 5-methyl-nicotinamide (200 g), Pd(OH)$_2$/C (20 wt %, 55 g), and 2 L of formic acid under a gentle steam of nitrogen. The autoclave was closed and flushed 3 times with nitrogen and 2 times with hydrogen under a continuous stirring. The hydrogenation reaction, performed at 40° C. under a H$_2$-pressure of 20 bar, was stirred until completion. Subsequently, the reaction mixture was filtered and concentrated to give 520 g of a crude product. The trans:cis ratio of the crude product was determined to be 85:15.

The crude product was dissolved in 3 L of 2-propanol and treated dropwise with a 1M solution of hydrochloric acid in diethyl ether. A hydrochloride salt was formed and isolated. Results from NMR analysis of the salt follow:

$^1$H-NMR (DMSO-d6, 400 MHz) ppm: 8.61 (br s, 2H), 7.74 (br s, 1H), 7.25 (br s, 1H), 3.23, 3.03 (ABq, J=11.0 Hz, 2H), 2.85 (d, J=11.6 Hz, 1H), 2.75-2.77 (m, 1H), 2.53-2.56 (m, 1H), 1.85-1.92 (m, 2H), 1.48-1.55 (m, 1H), 0.91 (d, J=6.3 Hz, 3H); $^{13}$C-NMR (DMSO-d6, 75 MHz) ppm: 175.27, 48.30, 43.62, 35.11, 32.84, 25.02, 18.05; MS(ESI): m/z=165.1 (M+Na$^+$).

Example 3: Stereoselective Hydrogenation of 5-methyl-nicotinamide in the Presence of HCl, H$_2$O/MeOH, and Pd/C

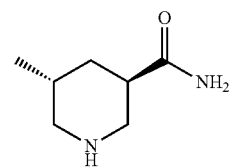

An autoclave was charged with 5-methyl-nicotinamide (15.6 g), hydrochloric acid (1.0 equivalent), H$_2$O (40 mL), MeOH (56 mL), and Pd/C (10 wt % on C, 0.5 g) under a gentle steam of nitrogen. The autoclave was closed and flushed 3 times with nitrogen and 2 times with hydrogen under a continuous stirring. The hydrogenation reaction was performed at 25° C. under a H$_2$-pressure of 20 bar and constant stirring. Subsequently, the reaction mixture was filtered and washed with H$_2$O/MeOH. The filtrate was concentrated and dried under vacuum to give a trans-isomeric piperidine with a trans:cis ratio of 89:11.

Example 4: Optical Resolution with (S)-(+)-Naproxen

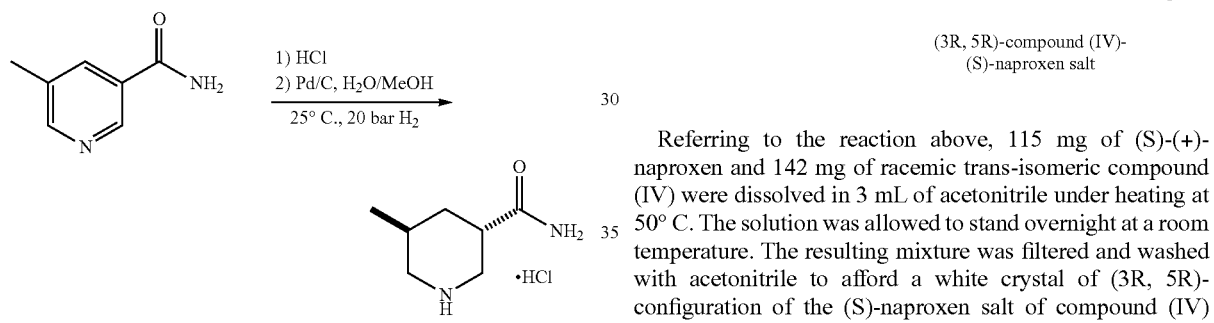

Referring to the reaction above, 115 mg of (S)-(+)-naproxen and 142 mg of racemic trans-isomeric compound (IV) were dissolved in 3 mL of acetonitrile under heating at 50° C. The solution was allowed to stand overnight at a room temperature. The resulting mixture was filtered and washed with acetonitrile to afford a white crystal of (3R, 5R)-configuration of the (S)-naproxen salt of compound (IV) (yield 43%; ee value 90%).

Example 5: Optical Resolution with (R)-(−)-Naproxen

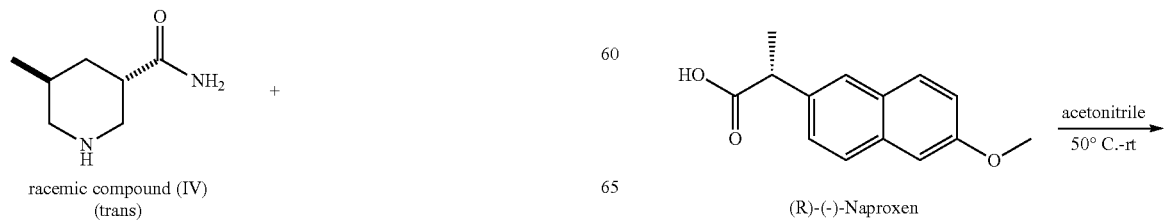

-continued

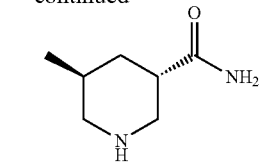

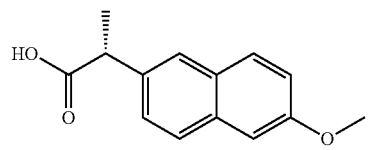

(3S, 5S)-compound (IV)-
(R)-naproxen salt

Referring to the reaction above, 1.26 g of (R)-(−)-naproxen and 1.56 g of racemic trans-isomeric compound (IV) were dissolved in 22 mL of acetonitrile under heating at 50° C. The solution thus obtained was allowed to stand overnight at a room temperature. The resulting mixture was filtered and washed with acetonitrile to afford a crystal of (3S, 5S)-configuration of the (R)-naproxen salt of compound (IV) (yield 42%; ee value 96.8%). The crystal was also recrystallized from acetonitrile and isopropanol (yield 66.7%; ee value 99.9%). Results from NMR analysis of the salt follow:

$^1$H-NMR (methanol-d4, 300 MHz) ppm: 7.61 (d, J=2.7 Hz, 1H), 7.58 (d, J=2.7 Hz, 1H), 7.41 (m, 0.5H), 7.38 (m, 0.5H), 7.08 (m, 1H), 7.00 (d, J=2.4 Hz, 0.5H), 6.97 (d, J=2.4 Hz, 0.5H), 3.78 (s, 3H), 3.62 (q, J=7.2 Hz, 1H), 3.21-3.24 (m, 2H), 2.95-3.00 (m, 1H), 2.67-2.73 (m, 2H), 2.30 (t, J=12.0 Hz, 1H), 1.79-1.88 (m, 2H), 1.36 (d, J=7.5 Hz, 3H), 1.34-1.35 (m, 1H), 0.78 (d, J=6.6 Hz, 3H); $^{13}$C-NMR (methanol-d4, 75 MHz) ppm: 183.43, 178.88, 158.86, 140.66, 134.93, 130.61, 130.26, 128.10, 127.80, 126.65, 119.68, 111.53, 106.67, 55.83, 50.97, 45.83, 37.43, 34.96, 26.84, 20.01, 18.75; MS (ESI): m/z=165.1 (M$^+$+Na).

OTHER EMBODIMENTS

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a series of equivalent or similar features.

From the above description, one skilled in the art can easily ascertain the essential characteristics of the present invention, and without departing from the spirit and scope thereof, can make various changes and modifications of the invention to adapt it to various usage and conditions. Thus, other embodiments are also within the scope of the following claims.

What is claimed is:

1. A trans-isomeric compound of formula (I) below or a pharmaceutically acceptable salt thereof:

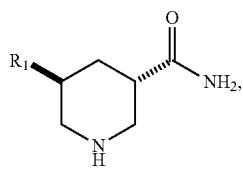

(I)

wherein $R_1$ is $C_1$-$C_5$ alkyl or $C_3$-$C_5$ cycloalkyl and the trans-isomeric compound has a trans:cis ratio of at least 70:30.

2. The compound of claim 1, wherein $R_1$ is $C_1$-$C_5$ alkyl.

3. The compound of claim 2, wherein $R_1$ is methyl.

4. The compound of claim 1, wherein the compound is present in the form of (3S, 5S)-configuration of formula (Ia) below or a pharmaceutically acceptable salt thereof:

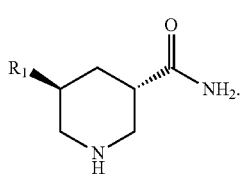

(Ia)

5. The compound of claim 1, wherein the compound is present in the form of (3R, 5R)-configuration of formula (Ib) below or a pharmaceutically acceptable salt thereof:

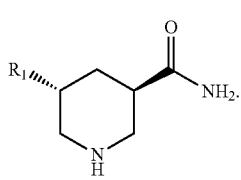

(Ib)

6. A method of preparing a trans-isomeric compound of formula (I) below or a pharmaceutically acceptable salt thereof:

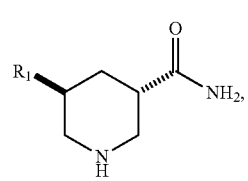

(I)

the method comprising hydrogenating a compound of formula (II) below or a pharmaceutically acceptable salt thereof:

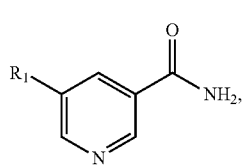

(II)

with a palladium catalyst in the presence of an inert solvent to obtain a trans-isomeric compound of formula (I) having a trans:cis ratio of at least 70:30 or a pharmaceutically acceptable salt thereof,
wherein $R_1$ of formulas (I) and (II) is $C_1$-$C_5$ alkyl or $C_3$-$C_5$ cycloalkyl.

7. The method of claim 6, further comprising a step of resolving the trans-isomeric compound or a pharmaceutically acceptable salt thereof with an acidic resolving agent to give an enantiomer of the trans-isomeric compound or a pharmaceutically acceptable salt thereof, wherein the enantiomer is present in the form of (3S, 5S)-configuration of formula (Ia) below or (3R, 5R)-configuration of formula (Ib) below:

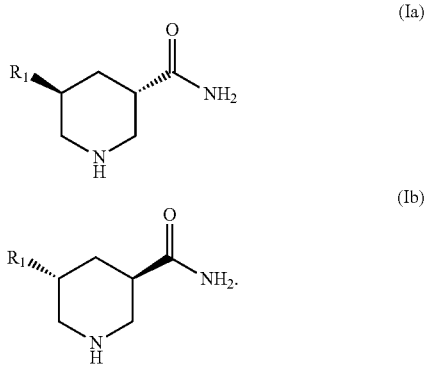

8. The method of claim 6, wherein $R_1$ is $C_1$-$C_5$ alkyl.

9. The method of claim 8, wherein $R_1$ is methyl.

10. The method of claim 6, wherein the palladium catalyst is $Pd(OH)_2/C$, Pd/C, $Pd(OAc)_2$, $Pd/Al_2O_3$, or a combination thereof, optionally containing Pt/C or Rh/C; and the content of palladium in the palladium catalyst is 0.01 wt % to 30 wt %.

11. The method of claim 6, wherein the inert solvent is $H_2O$, a $C_1$-$C_{10}$ ester, a $C_3$-$C_{10}$ cycloalkane, tetrahydrofuran (THF), dimethylformamide (DMF), acetonitrile, a $C_1$-$C_{10}$ alcohol, an alkylene glycol monoalkyl ether, an alkylene glycol monoalkyl ether carboxylate, an amide-based solvent, an organic acid, or a combination thereof, optionally combined with one or more inorganic acids.

12. The method of claim 11, wherein the inert solvent is $H_2O$, a $C_1$-$C_5$ ester, a $C_3$-$C_6$ cycloalkane, THF, DMF, a $C_1$-$C_5$ alcohol, propylene glycol monomethyl ether, propylene glycol monomethyl ether acetate, N,N-dimethylacetamide, a $C_1$-$C_5$ carboxylic acid, a $C_1$-$C_5$ sulfonic acid, or a combination thereof, optionally combined with hydrochloric acid.

13. The method of claim 12, wherein the inert solvent is $H_2O$, methanol, ethanol, isopropanol, formic acid, acetic acid, ethyl acetate, methanesulfonic acid, or a combination thereof, optionally combined with hydrochloric acid.

14. The method of claim 11, wherein the inert solvent is an organic acid or a combination of the organic acid with one or more solvents selected from the group consisting of $H_2O$, a $C_1$-$C_{10}$ ester, a $C_3$-$C_{10}$ cycloalkane, THF, DMF, acetonitrile, an alkylene glycol monoalkyl ether, an alkylene glycol monoalkyl ether carboxylate, an amide-based solvent, a $C_1$-$C_{10}$ alcohol, and an inorganic acid.

15. The method of claim 14, wherein the organic acid is formic acid, acetic acid, propionic acid, butyric acid, isobutyric acid, or a combination thereof.

16. The method of claim 7, wherein the acidic resolving agent is deoxycholic acid, (−)-2,3:4,6-di-o-isopropylidene-2-keto-L-gulonic acid monohydrate, D-(−)-quinic acid, L-pyroglutamic acid, (−)-monomethylsuccinate, N-acetyl-D-(+)-leucine, N-acetyl-L-methionine, (R)-(+)-N-(1-phenylethyl)succinamic acid, (S)-(+)-5-oxe-2-tetrahydrofurancarboxylic acid, (R)-(+)-N-(1-phenylethyl)phthalamic acid, (−)-mono-(1R)-menthyl phthalate, (−)-menthyloxyacetic acid, (S)-(+)-mandelic acid, L-(+)-tartaric acid, D-(+)-camphoric acid, (−)-dibenzoyl-L-tartaric acid anhydrous, (−)-dibenzoyl-L-tartaric acid monohydrate, (−)-O,O'-dibenzoyl-L-tartaric acid mono (dimethylamide), D-(+)-10-camphorsulfonic acid, L-(+)-lactic acid, L-(−)-malic acid, (−)-O,O'-di-p-toluoyl-L-tartaric acid, (R)-(−)-naproxen, (S)-ibuprofen, or a R-form or S-form thereof.

17. The method of claim 16, wherein the acidic resolving agent is deoxycholic acid, D-(−)-quinic acid, -(−)-monomethylsuccinate, N-acetyl-D-(+)-leucine, N-acetyl-L-methionine, (−)-mono-(1R)-menthyl phthalate, (−)-dibenzoyl-L-tartaric acid anhydrous, (−)-O,O'-dibenzoyl-L-tartaric acid mono(dimethylamide), D-(+)-10-camphorsulfonic acid, L-(+)-lactic acid, (R)-(−)-naproxen, or a R-form or S-form thereof.

18. The method of claim 7, further comprising a step of recrystallizing the (3S, 5S)-configuration or (3R, 5R)-configuration enantiomer with a recrystallization solvent.

19. The method of claim 18, wherein the recrystallization solvent is $H_2O$, a $C_1$-$C_{10}$ ester, a $C_3$-$C_{10}$ cycloalkane, THF, DMF, acetonitrile, a $C_1$-$C_{10}$ alcohol, or a combination thereof.

20. A trans-isomeric compound of formula (I) below or a pharmaceutically acceptable salt thereof:

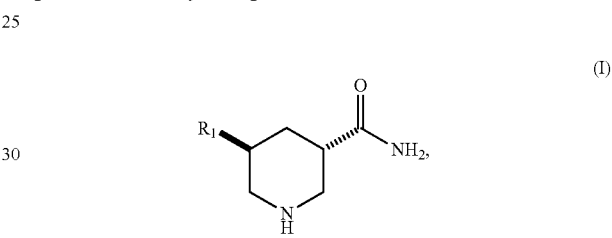

wherein the trans-isomeric compound having a trans:cis ratio of at least 70:30 is prepared by hydrogenating a compound of formula (II) below or a pharmaceutically acceptable salt thereof:

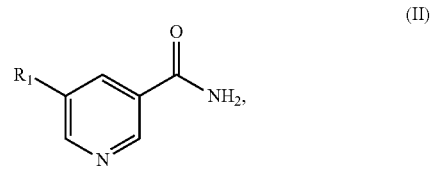

with a palladium catalyst in the presence of an inert solvent, in which $R_1$ of formulas (I) and (II) is $C_1$-$C_5$ alkyl or $C_3$-$C_5$ cycloalkyl.

21. The compound of claim 20, wherein $R_1$ is $C_1$-$C_5$ alkyl.

22. The compound of claim 21, wherein $R_1$ is methyl.

23. The compound of claim 20, wherein the compound is present in the form of (3S, 5S)-configuration of formula (Ia) below or (3R, 5R)-configuration of formula (Ib) below:

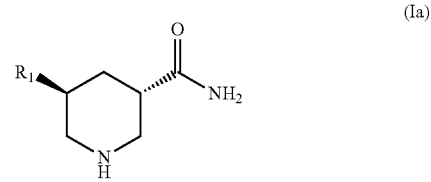

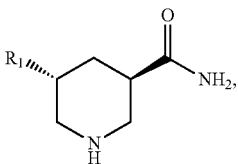
(Ib)

which is prepared via optical resolution of the trans-isomeric compound of formula (I) with an acidic resolving agent.

24. The compound of claim 20, wherein the palladium catalyst is Pd(OH)$_2$/C, Pd/C, Pd(OAc)$_2$, Pd/Al$_2$O$_3$, or a combination thereof, optionally containing Pt/C or Rh/C; and the content of palladium in the palladium catalyst is 0.01 wt % to 30 wt %.

25. The compound of claim 20, wherein the inert solvent is H$_2$O, a C$_1$-C$_{10}$ ester, a C$_3$-C$_{10}$ cycloalkane, THF, DMF, acetonitrile, a C$_1$-C$_{10}$ alcohol, an alkylene glycol monoalkyl ether, an alkylene glycol monoalkyl ether carboxylate, an amide-based solvent, an organic acid, or a combination thereof, optionally combined with one or more inorganic acids.

26. The compound of claim 25, wherein the inert solvent is H$_2$O, a C$_1$-C$_5$ ester, a C$_3$-C$_6$ cycloalkane, THF, DMF, a C$_1$-C$_5$ alcohol, propylene glycol monomethyl ether, propylene glycol monomethyl ether acetate, N,N-dimethylacetamide, a C$_1$-C$_5$ carboxylic acid, a C$_1$-C$_5$ sulfonic acid, or a combination thereof, optionally combined with hydrochloric acid.

27. The compound of claim 20, wherein the inert solvent is an organic acid or a combination of an organic acid with one or more solvents selected from the group consisting of H$_2$O, a C$_1$-C$_{10}$ ester, a C$_3$-C$_{10}$ cycloalkane, THF, DMF, acetonitrile, an alkylene glycol monoalkyl ether, an alkylene glycol monoalkyl ether carboxylate, an amide-based solvent, a C$_1$-C$_{10}$ alcohol, and an inorganic acid, in which the organic acid is formic acid, acetic acid, propionic acid, butyric acid, isobutyric acid, or a combination thereof.

28. The compound of claim 23, wherein the acidic resolving agent is deoxycholic acid, (−)-2,3:4,6-di-o-isopropylidene-2-keto-L-gulonic acid monohydrate, D-(−)-quinic acid, L-pyroglutamic acid, (−)-monomethylsuccinate, N-acetyl-D-(+)-leucine, N-acetyl-L-methionine, (R)-(+)-N-(1-phenylethyl)succinamic acid, (S)-(+)-5-oxe-2-tetrahydrofurancarboxylic acid, (R)-(+)-N-(1-phenylethyl)phthalamic acid, (−)-mono-(1R)-menthyl phthalate, (−)-menthyloxyacetic acid, (S)-(+)-mandelic acid, L-(+)-tartaric acid, D-(+)-camphoric acid, (−)-dibenzoyl-L-tartaric acid anhydrous, (−)-dibenzoyl-L-tartaric acid monohydrate, (−)-O,O'-dibenzoyl-L-tartaric acid mono (dimethylamide), D-(+)-10-camphorsulfonic acid, L-(+)-lactic acid, L-(−)-malic acid, (−)-O,O'-di-p-toluoyl-L-tartaric acid, (R)-(−)-naproxen, (S)-ibuprofen, or a R-form or S-form thereof.

* * * * *